(12) United States Patent
Nakada et al.

(10) Patent No.: US 6,767,348 B2
(45) Date of Patent: Jul. 27, 2004

(54) HIGH-FREQUENCY TREATMENT DEVICE

(75) Inventors: Mamoru Nakada, Hachioji (JP); Chika Shiro, Hachioji (JP)

(73) Assignee: Olympus Corporation, Tokyo (JP)

(*) Notice: Subject to any disclaimer, the term of this patent is extended or adjusted under 35 U.S.C. 154(b) by 198 days.

(21) Appl. No.: 10/115,603

(22) Filed: Apr. 3, 2002

(65) Prior Publication Data

US 2004/0054387 A1 Mar. 18, 2004

(51) Int. Cl.$^7$ .............................................. A61B 18/18
(52) U.S. Cl. ............................ 606/46; 606/51; 606/47
(58) Field of Search .......................... 606/41, 46–52, 606/205–208, 113, 114; 600/104

(56) References Cited

U.S. PATENT DOCUMENTS

| | | | | |
|---|---|---|---|---|
| 4,011,872 A | * | 3/1977 | Komiya | 606/47 |
| 4,418,692 A | * | 12/1983 | Guay | 606/42 |
| 5,667,525 A | * | 9/1997 | Ishibashi, deceased | 606/206 |
| 5,908,420 A | * | 6/1999 | Parins et al. | 606/51 |
| 6,482,205 B1 | * | 11/2002 | Bonnet | 606/51 |

FOREIGN PATENT DOCUMENTS

| | | |
|---|---|---|
| JP | 3-146046 | 6/1991 |
| JP | 5-11913 | 2/1993 |
| JP | 5-13410 | 2/1993 |
| JP | 2000-14678 | 2/2000 |

* cited by examiner

Primary Examiner—Michael Peffley
(74) Attorney, Agent, or Firm—Scully, Scott, Murphy & Presser

(57) ABSTRACT

A soft sheath and a pair of opening and closing elements which protrudes from and retracts into the soft sheath and is capable of opening and closing are provided in an insertion portion capable of being inserted through a treatment device insertion channel of an endoscope, a slender arm and a high-frequency surgical blade disposed at the distal end of the arm are formed in each opening and closing element, and a high-frequency treatment portion which converges a high-frequency current is provided on the blade.

8 Claims, 5 Drawing Sheets

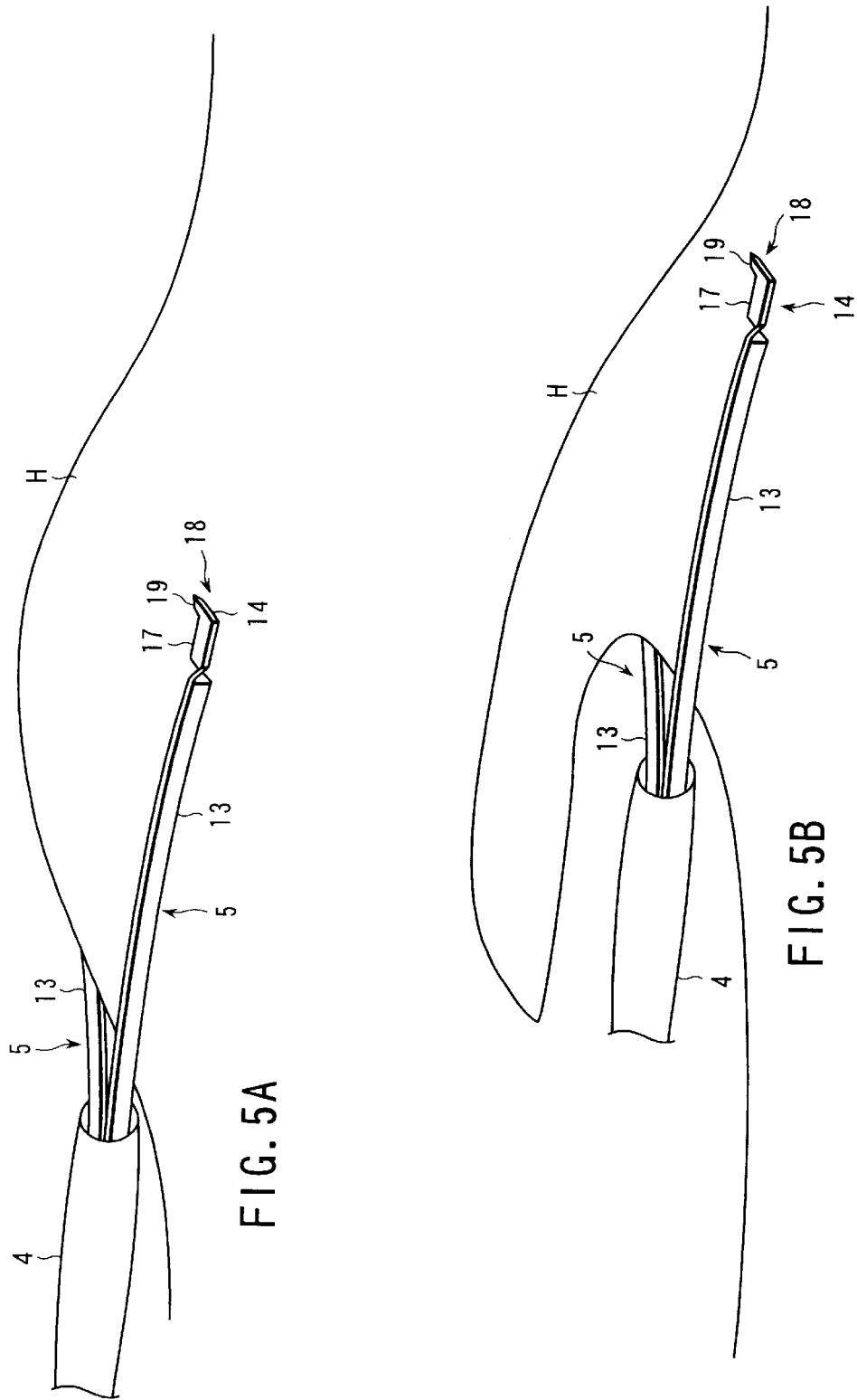

HIGH-FREQUENCY TREATMENT DEVICE

BACKGROUND OF THE INVENTION

1. Field of the Invention

The present invention relates to a high-frequency treatment device which is inserted into a body cavity through a channel of an endoscope and executes incision and excision of a mucous membrane in the body while delivering a high-frequency current.

2. Description of the Related Art

Devices that are inserted into a body cavity through the channel of the endoscope and execute incision and excision of living tissues in the body such as diseased mucous membranes include the following treatment devices. For example, a high-frequency snare is disclosed in Jpn. UM. Appln. KOKAI Publication No. 5-13410. A loop-shaped wire is provided at a distal end of an operation wire of the high-frequency snare. A living tissue is tied up with the loop-shaped wire, and the living tissue is excised while delivering a high-frequency current through the loop-shaped wire.

Jpn. Pat. Appln. KOKAI Publication No. 3-146046 discloses a pair of forceps with scissors. These forceps mechanically excise the living tissue by the shear force of a pair of scissors. Alternatively, Jpn. Pat. Appln. KOKAI Publication No. 2000-14678 discloses another high-frequency treatment device. This high-frequency treatment device can excise the living tissue by delivering a high-frequency current through a pair of partially insulated forceps.

Jpn. UM. Appln. KOKAI Publication No. 5-11913 discloses another high-frequency treatment device. This high-frequency treatment device is provided with a bipolar excision portion capable of closing and opening by protruding from and retracting into a distal end of a sheath. A pair of electrode members individually formed using a filament of wire is provided at the bipolar excision portion.

It is necessary for excising the living tissue such as the mucous membrane to confirm whether or not entire lesions are completely excised in order to prevent disease from recurring. For this purpose, it is required to reconstruct an excised piece to its original shape after the excision to confirm that the lesions are localized in the excised piece. Therefore, excision of the tissue takes a long time. An operation for excising a relatively large area of the living tissue is required for excising the entire lesions.

However, the entire lesions cannot be excised by a single operation with one attempt to excise a diseased mucous membrane having a wider area than the loop diameter using the high-frequency snare. Consequently, the living tissue should be excised in portions through plural operations. Not only does such repeated excision work require much time, but also the excised pieces may be dismembered. It is also difficult to precisely reassemble the dismembered excision pieces into their original shape after the excision. Accordingly, a treatment method capable of collectively excising a wide area of the mucous membrane, which is impossible by the high-frequency snare method, is required.

It is possible to proceed to cut the diseased mucous membrane little by little with a pair of forceps with scissors in order to collectively excise a wide area of the mucous membrane. The pair of forceps with scissors to be used herein is slender, and the operation wire for opening and closing the pair of scissors of the forceps is inserted through the sheath, which is required to be flexible. Accordingly, when the sheath is bent in an arbitrary shape during use such as in the case of the endoscope, the operational force of the operation wire in the bent sheath may not be sufficiently transferred to the pair of scissors. Since the shear force for incising the living tissue is not sufficiently imparted to the portion of the pair of scissors, the tissue cannot be sharply incised, thereby making the incision work itself difficult. In addition, the tissue may bleed since the living tissue is mechanically excised with the pair of forceps with scissors.

As a countermeasure for the problems above, one may attempt to perform incision by delivering a high-frequency current through the scissors part of the forceps. When the tissue is excised by the high-frequency current, the electric current must be converged on the incision area. However, when the contact area with the mucous membrane is large as encountered in the scissors of the forceps, a smooth incision may be impossible or it may be difficult to excise only the desired portion of the tissue with high accuracy due to divergence of the electric current.

Alternatively, the problem above may be solved by converging the high-frequency current on the tip of the blade by insulating portions of the forceps other than the tip of the blade. However, there occurs another problem in that the treatment device generates a high temperature by delivering the high-frequency current. In addition, since the scissors are in sliding contact with each other, a complicated and specified processing is required for applying an insulating coating on the scissors part. Therefore, the forceps with the scissors become very expensive.

It is also difficult to handle the incision portion with high accuracy by the method disclosed in Jpn. UM. Appln. KOKAI Publication No. 5-11913, because the wire used for the bipolar incision portion is so fine that the required elasticity cannot be obtained and the direction in which the pair of electrode members is opened is unstable. Furthermore, the opening width of such a treatment device is so narrow that a wide area of living tissue cannot be grasped. Therefore, a long time is required for excising a wide area of living tissue while making the incision work itself unstable.

BRIEF SUMMARY OF THE INVENTION

Accordingly, it is an object of the present invention, carried out considering the situations as hitherto described, to provide a high-frequency treatment device capable of collectively excising a living tissue such as a wide area of a mucous membrane safely and smoothly using an endoscope.

In order to achieve the above object, the present invention provides a high-frequency treatment device comprising a slender insertion portion to be inserted into a body cavity through a channel of an endoscope; an incision portion which is disposed at a distal end of the insertion portion and which executes incision and excision of a mucous membrane in the body while delivering a high-frequency current; and an operation portion which is disposed at a proximal end of the insertion portion and which manipulates the incision portion, wherein the insertion portion has a soft sheath and an operation wire inserted through the soft sheath to be movable in the axial direction. The incision portion has: a pair of opening and closing elements connected to the distal end of the operation wire and capable of opening and closing by protruding from and retracting into the distal end of the soft sheath, each opening and closing element having a slender and plate-shaped arm and a high-frequency surgical blade disposed at the distal end of the arm; and a high-frequency treatment portion which allows the high-frequency current to converge on the blade; and the operation portion comprises a switching member which switches from an opening operation position, at which the opening and closing elements are deformed into an open state which allows the blades of each opening and closing element to be separated from each other by protruding each opening and closing element from the distal end of the soft sheath by a push-out operation of the operation wire toward a distal side, to a closing operation position, at which the opening and closing elements are deformed into a closed state which allows the blades of each opening and closing element to close with each other by retracting each opening and closing element into the soft sheath by a pull-in operation of the operation wire in a proximal side, or vice versa.

Accordingly, in the present invention, when lesions are found by an observation with the endoscope, the insertion portion of the treatment device is inserted into the channel of the endoscope, and the treatment device is guided into the body cavity. After guiding the distal end of the insertion portion in the vicinity of the surface of the living tissue to be incised under observation with the endoscope, the opening and closing element is projected from the distal end of the soft sheath to open the opening and closing element. After pressing the opening and closing element onto the lesions to be excised while the element is open, the opening and closing element is closed by pulling the element into the sheath to grasp only the portion to be incised. A high-frequency current is then supplied to converge it on the high-frequency surgery part of the blade, thereby incising the mucous membrane. A wide area of lesions are completely excised as one block without dismembering the lesions.

Therefore, the present invention enables the living tissues such as a wide area of the mucous membrane to be collectively excised safely and smoothly; the addition the surgical operation is inexpensive.

Furthermore, the high-frequency treatment device according to the present invention has a small width portion in which the width of the blade is smaller than that of the arm. The lesions are sharply and reliably incised by converging a high-frequency current on the narrow part of the blade having a smaller width than the width of the arm during the high-frequency surgical operation.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5A is a perspective view showing the distal end of the incision device guided in the vicinity of a surface of a living tissue to be incised when the incision device according to the first embodiment is used;

FIG. 5B is a perspective view showing an incised state of the surface of the living tissue;

DETAILED DESCRIPTION OF THE INVENTION

Figure 1:
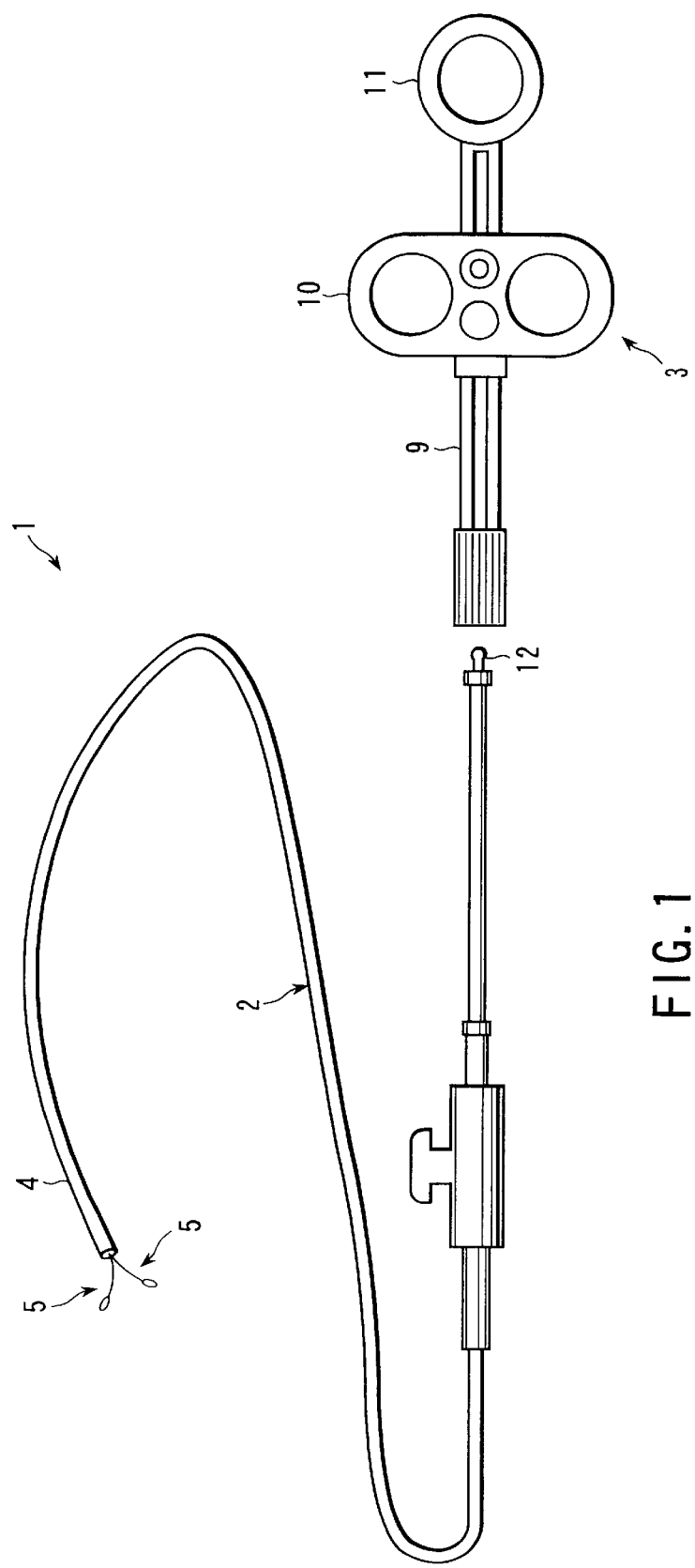
FIG. 1 is a plane view illustrating a schematic configuration of an incision device according to a first embodiment of the present invention.

A first embodiment of the present invention will be described hereinafter with reference to FIGS. 1 to 5B. FIG. 1 shows an incision device 1 as a high-frequency treatment device in the first embodiment. The incision device 1 is provided with a slender insertion portion 2 and a proximal handle 3. The slender insertion portion 2 can be inserted through a treatment device insertion channel of an endoscope (not shown). The proximal handle 3 is connected to a proximal end of the insertion portion 2 to be attachable and detachable. The insertion portion 2 of the incision device 1 is so constructed as to be able to be guided into a body cavity by taking advantage of the channel of the endoscope.

Figure 2:
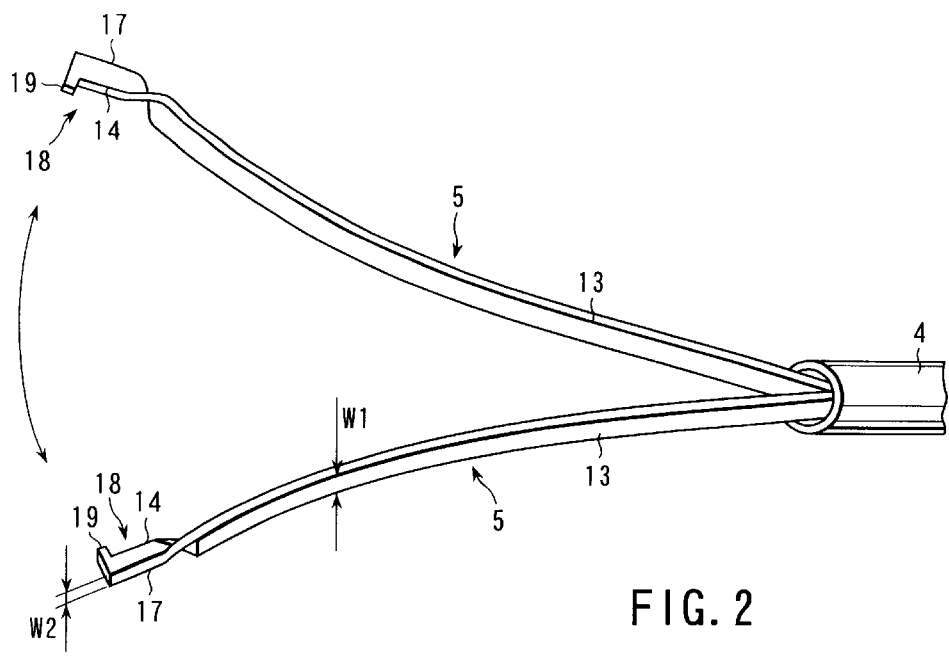
FIG. 2 is a perspective view showing an opening and closing element of the incision device according to the first embodiment.

As shown in FIG. 2, the insertion portion 2 also comprises, for example, a soft sheath 4 made of a synthetic resin and a pair of opening and closing elements 5 as arms. The soft sheath 4 is electrically insulated and flexible. The pair of opening and closing elements 5 is able to protrude from and retract into the distal end of the soft sheath 4 so as to enable opening and closing operation.

Figure 4A:
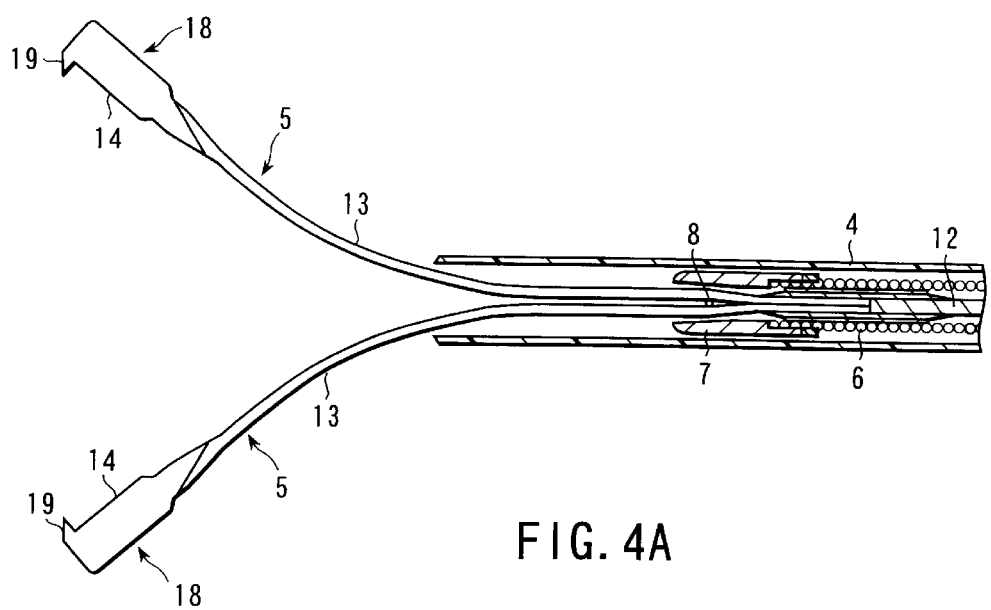
FIG. 4A is a vertical cross section of the main part showing an open state by protruding the opening and closing element from a distal end of a soft sheath in the excision device according to the first embodiment.
Figure 4B:
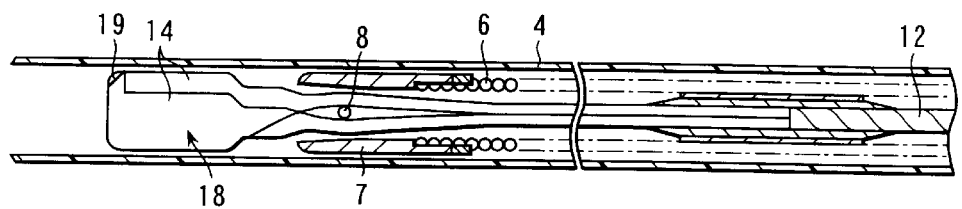
FIG. 4B is a vertical cross section of the main part showing a closed state by retracting the opening and closing element into the soft sheath.
Figure 4C:
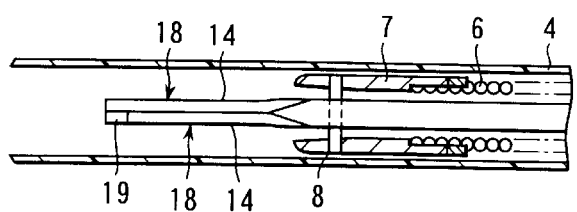
FIG. 4C is a vertical cross section of the main part when the incision device is rotated by 90° from the position shown in FIG. 4B.

A tightly wound coil 6 is disposed within the soft sheath 4 as shown in FIGS. 4A to 4C. A ring-shaped distal member 7 is fixed at the distal end of the coil 6. The distal member 7 is disposed at a pull-in position located at the back from the distal end position of the soft sheath 4.

A pin 8 is fixed to the distal member 7 as shown in FIG. 4C. This pin 8 is placed in the direction perpendicular to the center line direction of the sheath 4. The proximal end of the coil 6 is elongated to the handle 3 side.

The handle 3 is provided with a linear fixed axis 9 and a slider 10 as shown in FIG. 1. The slider 10 is mounted so that it is slidable in the axial direction along the fixed axis 9. A trigger ring 11 is formed at the terminal end of the fixed axis 9. The proximal end of the soft sheath 4 and the proximal end of the coil 6 are connected to the fixed axis 9 of the handle 3 while the handle 3 at the proximal side is connected to the proximal end of the insertion portion 2.

An operation wire 12 is inserted within the coil 6 to be freely movable in the axial direction. This operation wire 12 switches the pair of opening and closing elements 5 from an open state to a closed state or vice versa. The proximal end of the operation wire 12 is elongated toward the handle 3 side. The elongated part at the proximal end side of the operation wire 12 is connected to the slider 10 of the handle 3. A connection cable from a high-frequency power source (not shown) is connected to the slider 10. The proximal end of the operation wire 12 can be connected to the high-frequency power source via the slider 10 of the handle 3.

The pair of opening and closing elements 5 is connected to the distal end of the operation wire 12. Each opening and closing element 5 comprises a slender arm 13 and a monopolar type high-frequency surgical blade 14. The blade 14 is placed at the distal end of the arm 13.

Figure 3A:
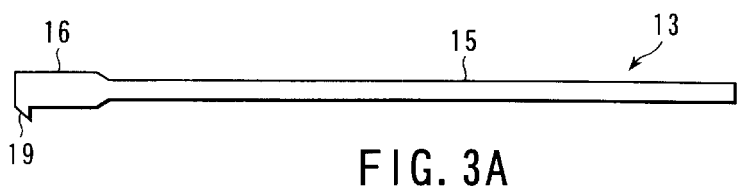
FIG. 3A is a plane view showing a base plate before forming a blade in a method of forming the blade of the opening and closing element of the incision device according to the first embodiment.
Figure 3B:
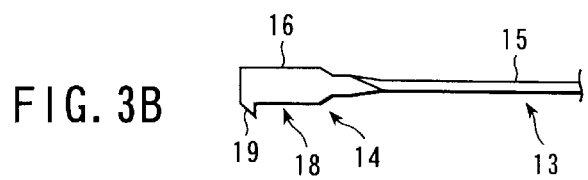
FIG. 3B is a side view showing the blade formed by 90° twist of a distal end of the base plate.

The arm 13 of each opening and closing element 5 is formed of a base plate 15 as shown in FIG. 3A. The base plate 15 is made of an approximately plate-shaped electroconductive material such as a metallic material, and has a rectangular cross section. A blade-shaped part 16 before forming the high-frequency surgical blade 14 is formed at the distal end of the base plate 15. The blade 14 is formed by about 90° of twist of the blade-shaped part 16 at the distal end of the base plate 15 as shown in FIG. 3B. As a result, a small width portion 17 where the width w2 of the blade 14 is smaller than the width w1 of the arm 13 is formed in the opening and closing element 5 as shown in FIG. 2. The small width portion 17 forms a high-frequency treatment portion 18 where the high-frequency current is converged on the blade 14.

A slide preventive projection 19 is formed within the distal end of each blade 14. The projection 19 catches the living tissue such as the mucous membrane, which can be incised by reliably holding the mucous membrane without sliding.

The pin 8 on the distal end member 7 is disposed between the arms 13 of the opening and closing elements 5 as shown in FIG. 4A. The proximal ends of the arms 13 of the opening and closing elements 5 pass through both sides of the pin 8, and are elongated toward the distal end of the operation wire 12. Planes of the base plates 15 at the proximal end of the arms 13 are joined together, and connected and fixed to the distal end of the operation wire 12. As a result, the pair of opening and closing elements 5 can simultaneously protrude from and retract into the distal end of the soft sheath 4 according to the advance/retract of the operation wire 12. At this time, the blades 14 of each opening and closing element 5 is deformed into an open state where the blades are allowed to be separated with each other, by allowing the opening and closing elements 5 to protrude from the distal end of the soft sheath 4 as shown in FIG. 4A. When each opening and closing element 5 is made to retract into the sheath 4 as shown in FIGS. 4B and 4C, on the other hand, the opening and closing elements 5 can be deformed into a closed state where the blades 14 of each opening and closing element 5 are closed with each other.

The dimension of the blade 14 is adjusted to be housed in the outer sheath 4 but not in the distal member 7 of the coil 6. Each opening and closing element 5 is pushed out from the distal end of the soft sheath 4 when the operation wire 12 is pushed out. The movement for deforming the opening and closing elements 5 in an open direction is enhanced during this push-out operation by the pin 8 between the opening and closing elements 5. The push-out length of each opening and closing element 5 when each opening and closing element 5 is pushed out from the distal end of the soft sheath 4 is regulated by the pin 8.

Each opening and closing element 5 retracts into the soft sheath 4 when the operation wire 12 is proximally pulled. The opening and closing elements 5 are deformed into a closed state where the blades 14 are closed with each other during this pull-in operation. The blades 14 of the pair of opening and closing elements 5 are simultaneously housed in the sheath 4 as shown in FIGS. 4B and 4C.

Rotation of each opening and closing element 5 around the axis of the sheath 4 relative to the coil 6 is regulated by the pin 8 on the distal member 7 of the coil 6, thereby fixing each opening and closing element 5 to be unable to rotate around the axis of the sheath 4. However, a clearance is provided between the coil 6 and the sheath 4. Therefore, the coil 6 is held to be able to freely rotate relative to the sheath 4 around the axis of the sheath 4. Consequently, no friction arises between the channel of the endoscope and the sheath 4 of the treatment device, when the pair of opening and closing elements 5 is in an open state and is pressed onto the mucous membrane. Therefore, the pair of opening and closing elements 5 can be automatically rotated in the direction around the axis together with the coil 6 to allow it to come into parallel contact with the mucous membrane.

The function of the above construction will be described hereinafter. The incision device 1 according to the present invention is used in combination with the endoscope. In other words, lesions in the body of a patient is previously inspected with the endoscope and, when a lesion to be incised is found, the insertion portion 2 of the incision device 1 is inserted through the channel of the endoscope to guide the incision device into the body cavity. The incision device 1 is maintained in a retracted state where the blades 14 of the pair of opening and closing elements 5 are housed in the sheath 4 during insertion as shown in FIGS. 4B and 4C.

After guiding the insertion portion 2 of the incision device 1 in the vicinity of the surface of the living tissue to be incised while observing with the endoscope, the slider 10 of the handle 3 is pushed out. As a result, the operation wire 12 is pushed out to protrude the opening and closing elements 5 from the sheath 4, thereby opening the opening and closing elements 5 as shown in FIG. 4A.

The opening and closing elements 5 are pressed onto the mucous membrane H while the elements are open as shown in FIG. 5A. A clearance is provided between the coil 6 and the sheath 4. Consequently, the coil 6 is held to be able to freely rotate around the axis of the sheath 4 relative to the sheath 4. Therefore, the pair of opening and closing elements 5 can be automatically rotated in the direction around the axis relative to the sheath 4 together with the coil 6 to allow it to come in parallel contact with the mucous membrane H.

The slider 10 of the handle 3 is pulled thereafter. The opening and closing element 5 is pulled into the sheath 4 by allowing the slider 10 to slide. Then, the opening and closing elements 5 close with each other while the mucous membrane H to be incised is grasped between the blades 14 of the two opening and closing elements 5. When a high-frequency current flows through the blades 14 of the two opening and closing elements 5, the portion of the mucous membrane H between the blades 14 of the two opening and closing elements 5 is incised.

After completing the incision, the mucous membrane is successively excised by repeating the same incision of the remaining mucous membrane H to be incised as shown in FIG. 5B. Consequently, the entire mucous membrane H at a wide area of lesion is completely excised as a block without dismembering the mucous membrane H at the wide area of the lesion.

The construction above exhibits the following effects. The excision device 1 comprises a main frame of the high-frequency treatment device, in which the high-frequency treatment portion 18 where a high-frequency current is converged on the blade 14 is provided. The main frame of the high-frequency treatment device comprises, at the insertion portion 2 capable of inserting into the treatment device insertion channel of the endoscope, the soft sheath 4 and the pair of opening and closing elements 5 that protrudes from and retracts into the distal part of the soft sheath 4 and is capable of opening and closing. In addition, a slender arm 13 and the high-frequency surgical blades 14 disposed at the distal end of the arm 13 are provided in each opening and closing element 5. Each opening and closing element 5 is deformed into am open state by allowing the blades 14 of the opening and closing elements 5 to separate with each other while each opening and closing element 5 protrudes from the distal end of the soft sheath 4. Otherwise, each opening and closing element 5 is deformed into a closed state by allowing the blades 14 of the opening and closing elements 5 to close with each other while allowing each opening and closing element 5 to retract into the soft sheath 4. Accordingly, the portion of the mucous membrane H between the blades 14 of the two opening and closing elements 5 can be sharply excised by passing a high-frequency current through the blades 14 of the two opening and closing elements 5, while only the mucous membrane H is grasped between the blades 14 of the two closed opening and closing elements 5.

When the mucous membrane H at a wide area of lesion is to be incised, the same incision work is repeatedly applied to the mucous membrane H at the wide area of lesion to successively incise the lesion. As a result, the entire mucous membrane H at a wide area of lesion is completely excised as one block without dismembering the lesions. Therefore, there is no possibility that the area that can be excised is restricted due to the dimension of the loop as seen when the high-frequency snare is used.

The high-frequency current is supplied to the blades 14 of the two opening and closing elements 5 in the incision device, according to this embodiment. Therefore, the portion of the mucous membrane H between he blades 14 of the two opening and closing elements 5 can be sharply excised.

It is difficult to mechanically excise the mucous membrane using a pair of scissors of the forceps, since the incision force is not sufficiently transferred to the tip of the scissors when the sheath of the soft treatment device is bent to a desired shape. In contrast, the incision device 1 according to this embodiment has an effect for efficiently excising the portion of the mucous membrane H to be incised as compared with using the pair of scissors of the forceps.

The incision device 1 in this embodiment has the slender arm 13 while having the high-frequency treatment portion 18 where the high-frequency current is converged on the blade 14. When a high-frequency treatment device by which the mucous membrane is incised by passing a high-frequency current through the scissors part of the forceps is used, smooth incision is impossible because the area of the portion that makes contact with the mucous membrane is so large that the electric current is diverged. On the contrary, the incision device 1 of this embodiment has an effect for sharply excising the portion of the mucous membrane H to be incised as compared with the scissors of the forceps. Furthermore, the incision device 1 can be cheaply manufactured in this embodiment by eliminating the need of applying an especially expensive insulation coating on the blade 14 of the incision device 1.

The arm 13 of each opening and closing element 5 is formed with the base plate 15 having a rectangular cross section as shown in FIG. 3A in this embodiment. In addition, the base plates 15 at the proximal end of each arm 13 are connected and fixed to the distal end of the operation wire 12 while the planes of the base plates are bonded with each other. The pin 8 of the distal end member 7 is placed between the arms 13 of the two opening and closing elements 5. Therefore, each arm 13 becomes flexible to ensure opening and closing while stabilizing the open direction.

The blade 14 of each opening and closing element 5 is formed by 90° twist of the arm 13. Consequently, the small-width portion 17 is formed in the each opening and closing element 5 as shown in FIG. 2 by making the width w2 of the blade 14 to be smaller than the width w1 of the arm 13. In other words, since the relation of w1>w2 is valid, the blade can tightly contact the mucous membrane H to enable the mucous membrane to be sharply and efficiently incised.

The projection 19 is formed within the blade 14 in this embodiment. As a result, the mucous membrane H is caught by this projection 19 when the portion of the mucous membrane H is grasped between the blades 14 of the two opening and closing elements 5, thereby enabling the mucous membrane H to be reliably held and incised without sliding.

Figure 6:
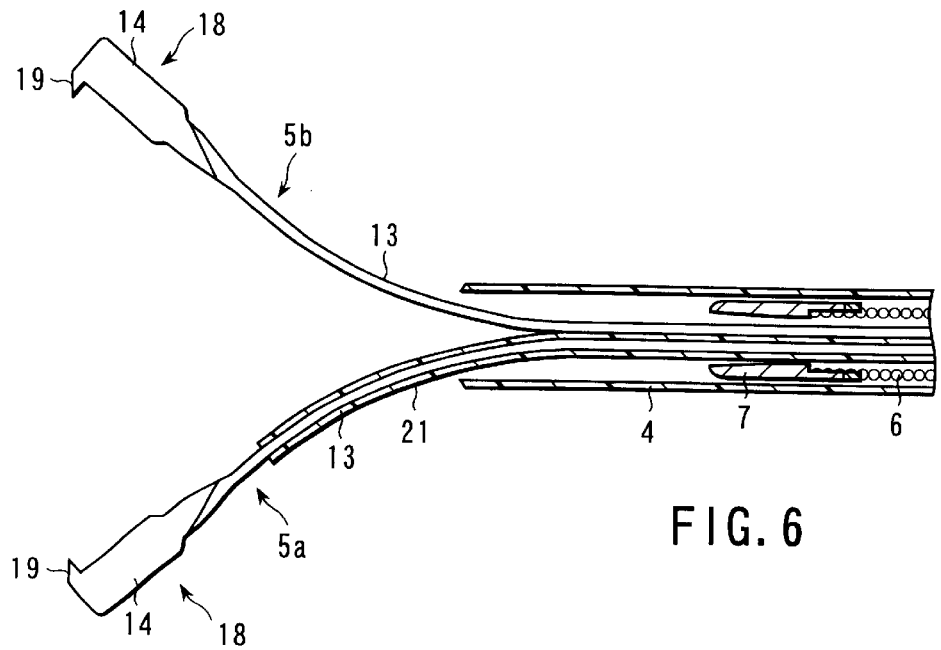
FIG. 6 is a vertical cross section of the main part showing an internal configuration of a distal end of an incision device according to a second embodiment of the present invention.

FIG. 6 shows a second embodiment of the present invention. The configuration of the incision device 1 of the first embodiment (FIGS. 1 to 5B) is changed in this embodiment as follows.

The outer periphery of the arm 13 of one opening and closing element 5a of the two opening and closing elements 5 is covered with an insulation tube 21. As a result, one opening and closing element 5a is insulated from the other opening and closing element 5b.

The operation wire 12 has two wire structures insulated with each other. The proximal end of the arm 13 of one opening and closing element 5a and the proximal end of the other arm 13 of the other opening and closing element 5b are connected to one wire construction and the other wire construction, respectively. As a result, high-frequency electric currents having different polarities with each other flow through the two opening and closing elements 5a and 5b, respectively. Bipolar type electrodes are formed on the blades 14 of the opening and closing elements 5a and 5b. Since the other portions of the incision device 1 in this embodiment have the same construction as that of the first embodiment, the same portions in this embodiment as those in the first embodiment are denoted by the same reference numerals, and descriptions thereof are omitted herein.

The outer periphery of the arm 13 of one opening and closing element 5a of the two opening and closing elements 5 is covered with the insulation tube 21 to insulate the opening and closing element 5a from the other opening and closing element 5b. Consequently, the bipolar type electrodes are formed on the blades 14 of the opening and closing elements 5a and 5b by passing high-frequency currents having different polarities from each other through the two opening and closing elements 5a and 5b, respectively. As a result, a short circuit is prevented from occurring by the insulation tube 21 of the arm 13 of one opening and closing element 5a, and the incision device 1 capable of sharp incision can be manufactured by the bipolar type electrodes. The outer periphery of the arm 13 of one opening and closing element 5a is covered with the insulation tube 21 in this embodiment. Since no technology for applying insulation coating on the arm 13 of the opening and closing element 5a is required, the incision device 1 has no possibility of being expensive.

Figure 7A:
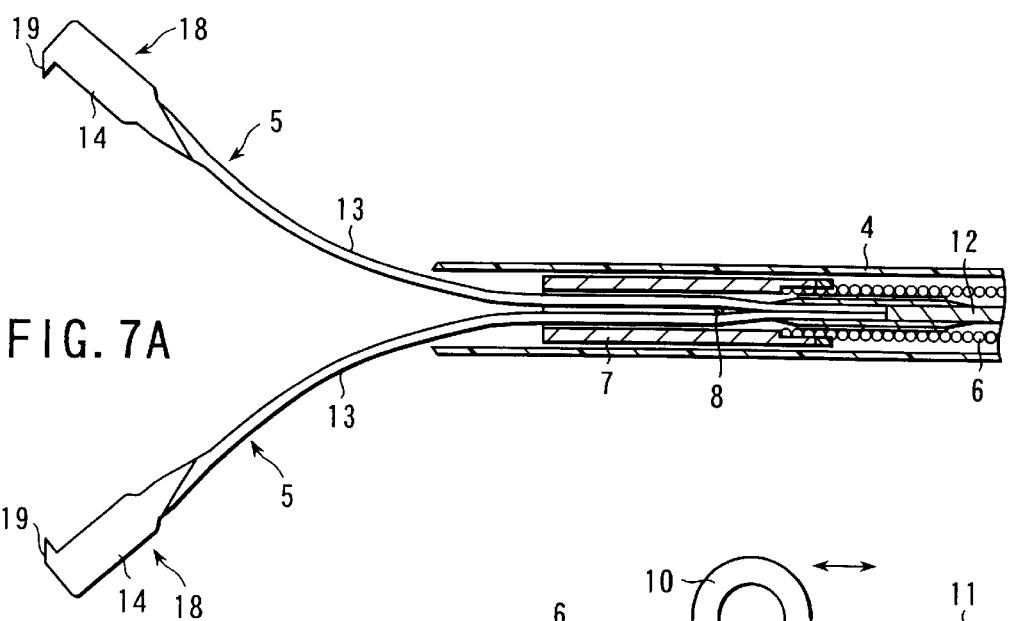
FIG. 7A is a vertical cross section of the main part showing an internal structure of a distal end of an incision device according to a third embodiment of the present invention.
Figure 7B:
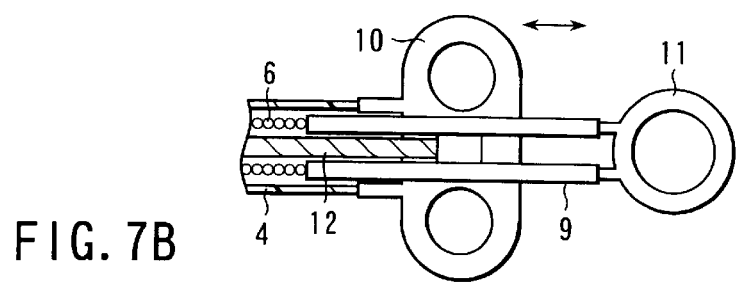
FIG. 7B is a vertical cross section of the main part showing a proximal operation portion of the incision device according to the third embodiment.

FIGS. 7A and 7B show a third embodiment of the present invention. The configuration of the incision device 1 in the first embodiment (see FIGS. 1 to 5B) is changed as follows in this embodiment.

The proximal end of the coil 6 is fixed to the fixing axis 9 of the handle 3 of the incision device 1. In addition, the proximal end of the soft sheath 4 and the proximal end of the operation wire 12 are fixed to the slider 10 of the handle 3. Since the other portions of the incision device 1 in this embodiment has the same construction as that of the first embodiment, the same portions in this embodiment as those in the first embodiment are denoted by the same reference numerals, and descriptions thereof are omitted herein.

The function of the construction above will be described hereinafter. The coil 6 is pushed out forward relative to the sheath 4 and the operation wire 12 in this embodiment by pulling the slider 10 of the handle 3 toward the proximal end. Consequently, the blades 14 of the two opening and closing elements 5 are closed with each other by allowing the arm 13 of each opening and closing element 5 to retract into the distal member 7 of the coil 6.

The coil 6 moves front and rear relative to the sheath 4 and operation wire 12 in the construction above when the slider 10 of the handle 3 is operated. Therefore, the frictional force applied between the sheath 4 and the channel of the endoscope can be reduced as compared with the first embodiment. As a result, changes of the positional relation between the opening and closing element 5 and the endoscope during the closing and opening operation of the opening and closing element 5 can be reduced as compared with the operation for pulling the two opening and closing elements 5 into the sheath 4 as seen in the first embodiment, when the desired mucous membrane is grasped between the blades 14 of the two opening and closing elements 5. Therefore, this construction can display an effect for more reliably grasping the desired portion of the mucous membrane.

It is needles to say that the present invention is not restricted to the embodiments above, and various modifications of the embodiment are possible within the scope not departing from the spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency treatment device comprising:
    a sheath;
    a pair of arm portions extending along a longitudinal axis of the sheath, each of the pair of arm portions comprising a plate-shaped arm including a planar portion and a small-width portion, the pair of arm portions being slidingly disposed in the sheath such that they are separated from each other when projected outward from the sheath and approach each other when retracted towards the sheath; and
    a pair of twist portions twisted around the longitudinal axis, each of the pair of twist portions being formed near a distal end portion of one of the pair of arm portions, wherein the small-width portion of each of the pair of twist portions face each other to form a blade for high-frequency treatment.

2. A high-frequency treatment device according to claim 1, wherein a small-width portion in which the width of the blade is smaller than the width of the arm is formed in the high-frequency treatment portion.

3. A high-frequency treatment device according to claim 1, wherein each of the pair of twist portions is twisted about 90° around the longitudinal axis.

4. A high-frequency treatment device according to claim 1, wherein the blade and the arm are integrated into an electroconductive member.

5. A high-frequency treatment device according to claim 1, wherein the blade has a slide preventive projection therewithin.

6. A high-frequency treatment device according to claim 1, wherein the incision portion is rotatable around the axis of the soft sheath.

7. A high-frequency treatment device according to claim 1, wherein the soft sheath is formed of a double sheath comprising an outer sheath and an inner sheath disposed at the inside of the outer soft sheath, and
    the inner sheath is able to protrude from and retract into the outer soft sheath.

8. A high-frequency treatment device according to claim 1, wherein at least one of the pair of opening and closing elements is insulated with an insulation member except the blade in the incision portion.

* * * * *